(12) United States Patent
Zhang et al.

(10) Patent No.: US 8,858,486 B2
(45) Date of Patent: Oct. 14, 2014

(54) METHOD AND ARRANGEMENT FOR DETERMINING THE RECIRCULATION IN A FISTULA OR THE CARDIOPULMONARY RECIRCULATION, AND A BLOOD TREATMENT DEVICE COMPRISING A DEVICE FOR DETERMINING THE FISTULA RECIRCULATION OR THE CARDIOPULMONARY RECIRCULATION PART

(75) Inventors: Wei Zhang, Niederwerrn (DE); Elke Schulte, Schweinfurt (DE); Christoph Bardorz, Rottendorf (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 607 days.

(21) Appl. No.: 12/744,281

(22) PCT Filed: Nov. 22, 2008

(86) PCT No.: PCT/EP2008/009917
§ 371 (c)(1),
(2), (4) Date: Sep. 9, 2010

(87) PCT Pub. No.: WO2009/065611
PCT Pub. Date: May 28, 2009

(65) Prior Publication Data
US 2011/0004141 A1    Jan. 6, 2011

(30) Foreign Application Priority Data
Nov. 22, 2007   (DE) .......................... 10 2007 056 475

(51) Int. Cl.
*A61M 37/00*   (2006.01)
*A61M 1/36*    (2006.01)
*A61M 1/16*    (2006.01)

(52) U.S. Cl.
CPC ............... *A61M 1/16* (2013.01); *A61M 1/3658* (2014.02); *A61M 1/1617* (2014.02); *A61M 2205/13* (2013.01)
USPC ....................................................... 604/6.09

(58) Field of Classification Search
USPC ......................................................... 604/6.09
See application file for complete search history.

(56) References Cited

U.S. PATENT DOCUMENTS 3,946,731 A * 3/1976 Lichtenstein .................. 604/66
4,702,829 A * 10/1987 Polaschegg et al. ....... 210/195.2
(Continued)

FOREIGN PATENT DOCUMENTS

DE    195 28 907    11/1996
DE    195 41 783     3/1997
(Continued)

OTHER PUBLICATIONS

PCT International Search Report for PCT/EP08/009917 mailed on Apr. 16, 2009.
(Continued)

Primary Examiner — Susan Su
Assistant Examiner — Guy K Townsend
(74) Attorney, Agent, or Firm — Kenyon & Kenyon LLP

(57) ABSTRACT

A method for determining the recirculation in a fistula and/or the cardiopulmonary recirculation part during an extracorporeal blood treatment is disclosed, where the blood to be treated flows in an extracorporeal blood circuit through a blood chamber of a dialyzer split by a semi-permeable membrane into the blood chamber and a liquid chamber, and dialysis liquid flows in a dialysis liquid path through the dialysis liquid chamber of the dialyzer. A device for determining the recirculation in a fistula and/or the cardiopulmonary recirculation part, and a blood treatment device including such a device are also disclosed. The method and device are based on the fact that the sum of the fistula recirculation and the cardiopulmonary recirculation part, i.e. the total recirculation, is determined for two blood flow rates which differ from each other. The fistula recirculation and/or the cardiopulmonary recirculation part are then determined from the recirculation for the two blood flow rates.

8 Claims, 2 Drawing Sheets

(56) References Cited

U.S. PATENT DOCUMENTS

| | | | | |
|---|---|---|---|---|
| 5,098,373 | A * | 3/1992 | Polaschegg | 604/6.05 |
| 5,507,723 | A * | 4/1996 | Keshaviah | 604/6.11 |
| 5,510,716 | A * | 4/1996 | Buffaloe et al. | 324/445 |
| 5,510,717 | A * | 4/1996 | Buffaloe et al. | 324/445 |
| 5,662,806 | A * | 9/1997 | Keshaviah et al. | 210/739 |
| 5,685,989 | A * | 11/1997 | Krivitski et al. | 210/646 |
| 5,716,531 | A * | 2/1998 | Kenley et al. | 210/746 |
| 5,830,365 | A * | 11/1998 | Schneditz | 210/739 |
| 5,866,015 | A | 2/1999 | Krämer | |
| 6,284,141 | B1 * | 9/2001 | Shaldon et al. | 210/739 |
| 6,537,240 | B2 | 3/2003 | Cavicchioli et al. | 604/5.01 |
| 6,702,774 | B1 | 3/2004 | Polaschegg | 604/5.01 |
| 7,001,353 | B2 * | 2/2006 | Bosetto et al. | 604/5.01 |
| 7,223,532 | B1 | 5/2007 | Nowak et al. | 435/2 |
| 7,285,105 | B2 * | 10/2007 | Kim et al. | 604/5.04 |
| 7,341,568 | B2 * | 3/2008 | Zhang | 604/4.01 |
| 7,699,992 | B2 * | 4/2010 | Sternby | 210/739 |
| 7,704,213 | B2 * | 4/2010 | Kraemer | 600/504 |
| 7,762,980 | B2 * | 7/2010 | Gertner | 604/43 |
| 7,815,809 | B2 * | 10/2010 | Jansson et al. | 210/746 |
| 7,850,856 | B2 * | 12/2010 | Zhang et al. | 210/741 |
| 2003/0083901 | A1 * | 5/2003 | Bosch et al. | 705/2 |
| 2003/0163077 | A1 * | 8/2003 | Kim et al. | 604/5.01 |
| 2004/0073153 | A1 * | 4/2004 | Bosetto et al. | 604/5.03 |
| 2005/0082226 | A1 * | 4/2005 | Bene et al. | 210/646 |
| 2005/0133449 | A1 * | 6/2005 | Sternby | 210/645 |
| 2006/0047193 | A1 * | 3/2006 | Zhang | 600/368 |
| 2006/0064025 | A1 * | 3/2006 | Kraemer | 600/504 |
| 2006/0200064 | A1 * | 9/2006 | Gross et al. | 604/5.01 |
| 2006/0254982 | A1 * | 11/2006 | Kopperschmidt | 210/646 |
| 2007/0131595 | A1 * | 6/2007 | Jansson et al. | 210/96.2 |
| 2008/0097272 | A1 * | 4/2008 | Daniel et al. | 604/6.09 |
| 2010/0276367 | A1 * | 11/2010 | Zhang | 210/647 |

FOREIGN PATENT DOCUMENTS

| | | |
|---|---|---|
| DE | 197 02 441 | 2/1998 |
| WO | WO 2006/072271 | 7/2006 |

OTHER PUBLICATIONS

Schneditz et al., 1999, "Validation of haemodialysis recirculation and access blood flow measured by thermodiluation", Nephrol Dial Transplant 14:376-383.

Kramer et al., 1993, "Automatische Messung der Rezirkulation", EDTNA-ERCA Journal vol. XIX, No. 2: 8-15. (with English translation).

International Preliminary Report on Patentability for PCT/EP08/009917 mailed on Jun. 10, 2010.

* cited by examiner

METHOD AND ARRANGEMENT FOR DETERMINING THE RECIRCULATION IN A FISTULA OR THE CARDIOPULMONARY RECIRCULATION, AND A BLOOD TREATMENT DEVICE COMPRISING A DEVICE FOR DETERMINING THE FISTULA RECIRCULATION OR THE CARDIOPULMONARY RECIRCULATION PART

FIELD OF THE INVENTION

The present invention relates to a method of determining recirculation in a fistula and/or the cardio-pulmonary proportion of recirculation, during the extra-corporeal treatment of blood in which the blood to be treated flows in an extra-corporeal blood circuit through a blood chamber of a dialyser which is divided into the blood chamber and a dialysis-fluid chamber by a semi-permeable membrane and dialysis fluid flows through the dialysis-fluid chamber of the dialyser on a path for dialysis fluid. The present invention also relates to an arrangement for determining recirculation in a fistula and/or the cardio-pulmonary proportion of recirculation and to a blood-treating apparatus having an arrangement for determining fistular recirculation and/or the cardio-pulmonary proportion of recirculation.

BACKGROUND

In processes employed in chronic blood-cleansing therapy, such as hemodialysis, hemofiltration, and hemodiafiltration, blood is conveyed through an extra-corporeal blood circuit. As an access to the blood vessel system, an arteriovenous fistula is often made by an operation. Also possible is the use of an implant. When a "fistula" is mentioned below, what is meant by this is any kind of connection between a vein and an artery of the patient.

The blood flowing through the fistula is only used during the actual dialysis treatment. In the period during which there is no dialysis, the flow of blood in the fistula is equivalent to a functional left/right shunt in which a proportion of the arterial blood produced by the cardiac output is fed directly to the venous system and the heart and does not undergo any peripheral use. The fistular flow recirculates via the heart and lungs. The fractional proportion which the fistular flow represents of the cardiac output is defined as cardio-pulmonary recirculation. The cardio-pulmonary recirculation affects not only the load on the patient's circulation but also the efficiency of the dialysis. Because the dialyzed blood from the extra-corporeal circuit is mixed with the venous return from the greater circulation while bypassing the systemic areas of the circulation, there is a systematic reduction in the concentration of dialyzable constituents in the arterial blood (See D. Schneditz et al.: Cardiopulmonary recirculation during hemodialysis. Kidney Int. 42: 1450-1456, 1992).

For the ability of the fistula to work properly, its perfusion is an important factor. If the fistular flow drops below a critical level, there is an increased risk of a fistular thrombosis and the possible loss of the vascular access, which constitutes a major complication in dialysis treatment (See W. Bay et al.: Color Doppler flow predicts PTFE graft failure, J. Am. Soc. Nephrol. 5: 407 (1994)). If the fistular flow during the dialysis treatment is less than the extra-corporeal blood flow ($Q_B$), local fistular recirculation occurs, in which a fraction of the dialyzed blood which is fed back to the fistula by the venous blood line is fed back to the dialyser via the arterial blood line. The fistular recirculation ($R_A$) causes a significant reduction in the efficiency of dialysis (See F. Gotch: "Models to predict recirculation and its effect on treatment time in single-needle dialysis" First Intl. Symposium on Single-Needle Dialysis, Editors: S. Rignoir, R. Vanholder and P. Ivanovich, Cleveland, ISAO Press, 1984, page 305 ff). Measurement of the quality of the vascular access is thus an important way of ensuring quality in dialysis treatment.

Because of its clinical importance, there are various known methods of measuring recirculation. Common to all of them is the measurement of a physical or chemical parameter of the blood which is changed in the venous segment of the extra-corporeal circuit. The physical or chemical parameter of the blood can be changed by manually injecting an indicator or even indirectly via the dialysis treatment unit.

Where there is mention below of recirculation (R), fistular recirculation ($R_A$) or the cardio-pulmonary proportion of recirculation ($R_{CP}$), what these terms should be understood to mean are not absolute quantities but the proportions which the respective types of recirculation represent of the cardiac output. In practice, relative quantities are enough to enable the recirculation processes taking place in the fistula to be assessed.

A method of measuring recirculation which is called thermodilution is known from the EDTNA-ERCA Journal 19, 6 (1993). In this known method, a brief drop in temperature is initiated in the dialysis-fluid circuit and this is transmitted to the venous segment of the extra-corporeal circuit and produces a detectable sudden change in temperature in the arterial segment of the extra-corporeal circuit when recirculation is occurring.

A known arrangement for carrying out the method called thermodilution has a temperature sensor arranged in the arterial segment of the extra-corporeal circuit and a temperature sensor arranged in its venous segment. The venous temperature sensor senses the sudden change in temperature which is attributable to the drop in temperature caused in the dialysis-fluid circuit. The sudden change in temperature which is measured is analyzed and is then compared with the temperature curve registered at the arterial sensor. The ratio of the two integrals for temperature to one another, or the ratio between their amplitudes, is a measure of the overall reduction in the efficiency of the dialysis treatment caused by fistular and cardio-pulmonary recirculation.

The known arrangement for measuring recirculation has proved successful in practice. However, something that has been found to be a disadvantage is that it is only possible to measure the total recirculation, which will be referred to below as recirculation (R), which is the sum of fistular recirculation ($R_A$) and a proportion which derives from the cardio-pulmonary recirculation, which will be referred to below as the cardio-pulmonary proportion of recirculation ($R_{CP}$). A distinction must be made in this case between the cardio-pulmonary proportion of recirculation ($R_{CP}$) and the proportion of fistular flow in the cardiac output, which will be referred to below as the cardio-pulmonary recirculation ($R_{cp}$).

That method of measuring the total recirculation made up of fistular recirculation and cardio-pulmonary recirculation which is referred to as thermodilution is also described in Drukker, Parsons and Maher, Replacement of Renal Function by Dialysis, $5^{th}$ edition, 2004, Kluwer Academic Publishers BV.

A method of measuring recirculation (R), i.e., the sum of fistular recirculation ($R_A$) and the cardio-pulmonary proportion of recirculation ($R_{CP}$), is known from German Patent Publication No. DE 197 02 441 C1. In this known method, a physical or chemical parameter of the dialysis fluid is changed, along the path followed by the dialysis fluid, upstream of the dialyzer, and this causes a change in the physical or chemical parameter on the blood side. The change in the parameter of the dialysis fluid on the blood side results in a change in the parameter of the dialysis fluid downstream of the dialyzer. To determine recirculation, the parameter on the path followed by the dialysis fluid is measured downstream of the dialyzer and recirculation (R) is determined from the curve followed over time by the change in the parameter. What may be changed and measured as a physical or chemical parameter is the ion concentration in the dialysis fluid, such example as the Na concentration in the dialysis fluid, or even the temperature of the dialysis fluid. However, something that is disadvantageous is, once again, that what can be determined by the known method is not fistular recirculation or cardio-pulmonary recirculation but only recirculation as a whole.

German Patent Publication No. DE 195 28 907 C1 describes a method of determining cardio-pulmonary recirculation. The measurement of cardio-pulmonary recirculation is based on two measurements of the recirculation fraction which follow closely on one another and which are carried out automatically before and after the reversal of the blood flow. It is a disadvantage that this known method calls for the blood flow to be reversed.

U.S. Pat. No. 6,537,240 B2 describes a method of determining recirculation in which the ultrafiltration rate is changed and before and after the change in the ultrafiltration rate a value is determined for a blood parameter which is representative of the ratio of the volume of blood plasma to the volume of blood.

An object underlying the present invention is to specify a method which allows fistular recirculation and/or cardio-pulmonary recirculation to be determined during extra-corporeal blood treatment without the flow of blood in the extra-corporeal blood circuit being reversed.

A further object of the present invention is to provide an arrangement for determining fistular recirculation and/or cardio-pulmonary recirculation without the flow of blood being reversed.

Furthermore, it is an object of the present invention to provide a blood-treating apparatus which allows fistular recirculation and/or cardio-pulmonary recirculation to be determined without the flow of blood being reversed.

SUMMARY

The method according to the invention and the arrangement according to example embodiments of the invention are based on determining the sum of fistular recirculation ($R_A$) and the cardio-pulmonary proportion of recirculation ($R_{CP}$), i.e., recirculation (R) for two different blood flow rates which differ from one another. Fistular recirculation and/or cardio-pulmonary recirculation are then determined from the recirculations at the two blood flow rates.

For the method according to the present invention and the arrangement according to the present invention, it is immaterial by what method and by what arrangement the sum of fistular recirculation and the cardio-pulmonary proportion of recirculation is determined. Recirculation at the two blood flow rates can therefore be determined by known methods and by known arrangements.

It is of advantage if the measurements for determining recirculation for the subsequent calculation of fistular recirculation and cardio-pulmonary recirculation are not made invasively. The method of measuring recirculation which is known as thermodilution is therefore an obvious candidate (See EDTNA-ERCA Journal 19, 6 (1993)).

When it is a question of determining fistular recirculation and/or the cardio-pulmonary proportion of recirculation for two blood flow rates, this does not mean that fistular recirculation and/or the cardio-pulmonary proportion of recirculation cannot be determined from the recirculation at more than two blood flow rates. For example, a plurality of successive measurements may be made and means may be formed.

The first measurement of recirculation takes place at a high blood flow ($Q_{BH}$) at which fistular recirculation may occur, whereas the second measurement is made at a low blood flow ($Q_{BL}$) at which fistular recirculation does not occur. These two measured values form the basis for determining fistular recirculation and/or cardio-pulmonary recirculation.

The method according to the present invention and the arrangement according to the present invention make provision for fistular recirculation and/or the cardio-pulmonary proportion of recirculation to be calculated on the basis of an equation which contains, as terms, the blood flow ($Q_{BH}$) at the first measurement and the blood flow ($Q_{BL}$) at the second measurement, and the values determined for recirculation at the first and second measurements ($R_H$ and $R_L$ respectively).

Laboratory measurements show that fistular recirculation and/or the cardio-pulmonary proportion of recirculation can be calculated with great accuracy by the method according to the invention.

The arrangement according to the invention for determining fistular recirculation and/or the cardio-pulmonary proportion of recirculation has a means of changing a physical or chemical parameter in the blood and a means of measuring the change in the physical or chemical parameter in the blood. The physical or chemical parameter may for example be the concentration of a substance in the blood or the temperature of the blood. It is preferably the temperature of the blood that is changed. The change in the temperature of the blood is preferably made by changing the temperature of the dialysis fluid, in which case the temperature bolus propagates from the dialysis-fluid side via the dialyser to the blood side.

The arrangement according to the invention also has a computing and analyzing unit which is so designed that fistular recirculation and/or the cardio-pulmonary proportion of recirculation can be determined on the basis of the physical or chemical parameter which is measured at a first and a second blood flow rate.

In a preferred embodiment of the arrangement according to the invention, the means of changing the physical or chemical parameter in the blood is a means of changing the temperature of the blood and the means of measuring the physical or chemical parameter in the blood is a means of measuring the temperature of the blood.

The arrangement according to the invention for determining fistular recirculation and/or the cardio-pulmonary proportion of recirculation may form a separate sub-assembly or may be part of the blood-treating apparatus, which latter has an extra-corporeal blood circuit having a dialyzer which is divided into a blood chamber and a dialysis-fluid chamber by a semi-permeable membrane.

An embodiment of the invention will be explained in detail below by reference to the drawings.

DETAILED DESCRIPTION

Figure 1:
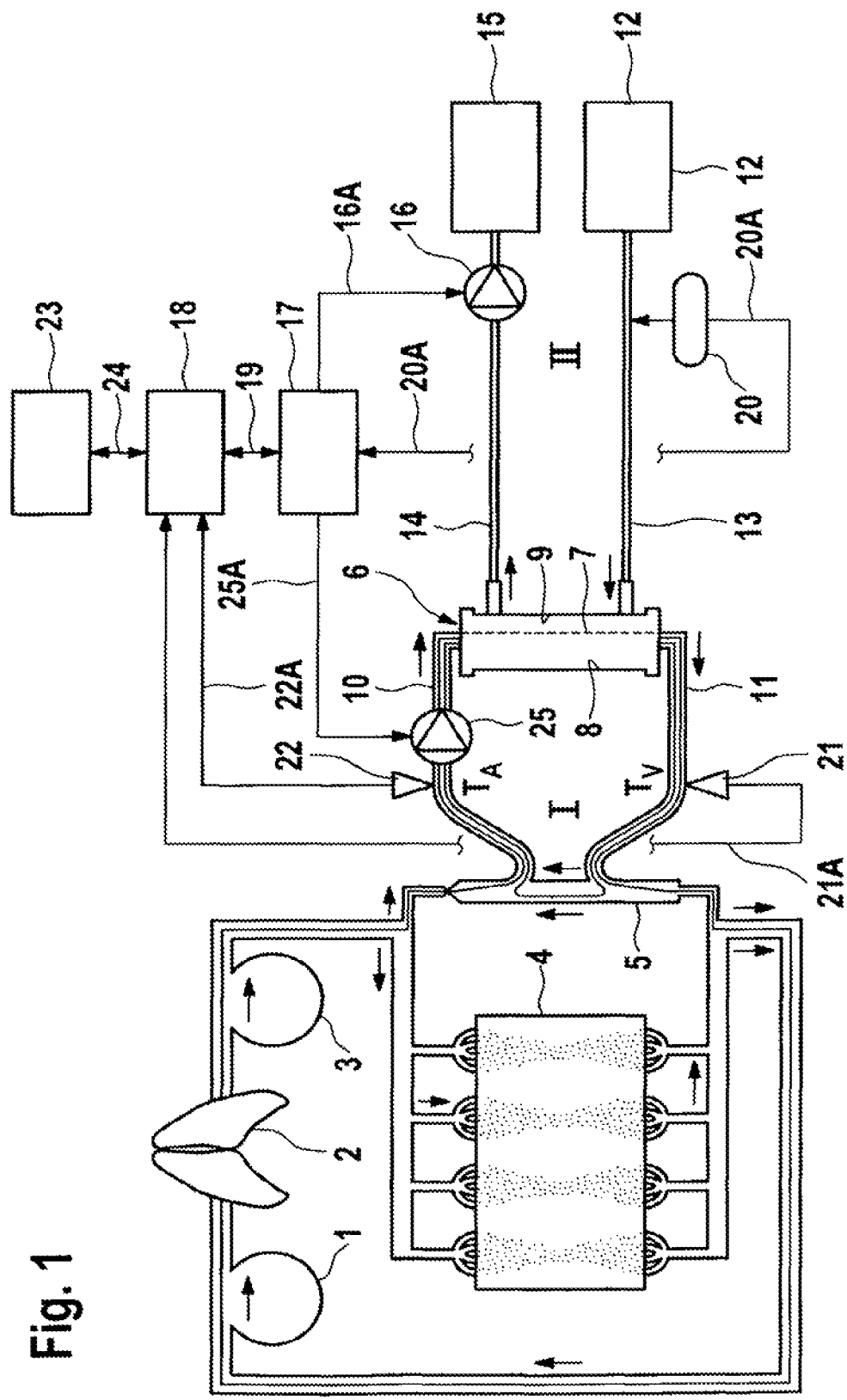
FIG. 1 is a schematic view of the arrangement according to the invention for determining fistular recirculation and/or the cardio-pulmonary proportion of recirculation together with a blood-treating apparatus, including the intra-corporeal blood circuit.

In the present example embodiment, the arrangement for determining fistular recirculation and/or the cardio-pulmonary proportion of recirculation is part of the extra-corporeal blood-treating apparatus, with the arrangement for determining the proportions of recirculation making use of some of the components of the dialysis apparatus.

The intra-corporeal circuit comprises the right ventricle 1 of the heart, the lungs 2, the left ventricle 3 and all the capillary systems 4 of the internal organs, the musculature and the skin etc. To give access to the blood vessel, an arteriovenous fistula 5 is made.

The dialysis apparatus has a dialyzer 6 which is separated into a blood chamber 8 and a dialysis-fluid chamber 9 by a semi-permeable membrane 7. Running from the arterial part of the fistula 5 via an arterial connection (not shown) is an arterial blood line 10 which leads to an inlet to the blood chamber 8 and running from an outlet of the blood chamber 8 of the dialyzer 6 is a venous blood line 11 which leads, via a venous patient connection (not shown), to the venous part of the fistula 5. Arranged in the arterial blood line 10 is a blood pump 25 which pumps the blood in the extra-corporeal blood circuit I at a preset blood flow rate.

The dialysis fluid is supplied by a means 12 from which a dialysis-fluid infeed line 13 leads to an inlet to the dialysis-fluid chamber 9, while a dialysis-fluid takeaway line 14 in the path II for the dialysis fluid leads from an outlet from the dialysis-fluid chamber 9 of the dialyzer 6 to an outlet 15. Connected into the dialysis-fluid takeaway line 14 is a dialysis-fluid pump 16.

The dialysis apparatus has a central control unit (microprocessor) 17 which is connected via control lines 25A and 16A to the blood pump 25 and the dialysis-fluid pump 16. The control unit 17 presets the pumping rates of the pumps 25, 16 and a given blood flow rate $Q_B$ thus becomes established in the extra-corporeal blood circuit I and a given dialysis-fluid rate $Q_D$ in the path II for the dialysis fluid.

The arrangement for determining fistular recirculation and/or the cardio-pulmonary proportion of recirculation has a computing and analyzing unit 18 which is connected to the central control unit 17 by a data line 19. The arrangement also has a means 20 of changing a physical or chemical parameter in the blood. In the present embodiment, the means 20 is a means by which the temperature in the blood is changed for a brief period. This brief change in temperature in the blood is referred to as a temperature bolus.

In the present embodiment, the means 20 produces a temperature bolus, in the path II for the dialysis fluid, upstream of the dialysis-fluid chamber 9 of the dialyzer 6. To produce the temperature bolus, the temperature of the dialysate is typically raised or lowered by approximately 2.5° C. for 2.5 minutes, before then being restored to the original value. The means 20 for producing the temperature bolus is connected by a control line 20A to the control unit 17 of the dialysis apparatus.

Serving to detect the change in the physical or chemical parameter on the blood side is a means which comprises a non-invasive venous temperature sensor 21 for measuring the venous blood temperature $T_V$ and a non-invasive arterial temperature sensor 22 for measuring the arterial blood temperature $T_A$. The venous and arterial temperature sensors 21, 22 are connected to the computing and analyzing unit 18 by data lines 12A and 22A.

In what follows, the way in which the dialysis apparatus works will be explained in further detail.

The major part of the blood pumped out by the left ventricle 1 flows into the capillary systems of all the organs and a small part flows into the fistula 5. In the event that the blood flow in the extra-corporeal circuit is less than the flow of the blood flowing into or out of the fistula, one part of the fistular blood flows through the extra-corporeal blood circuit I and the other part through the fistula 5. The extra-corporeal blood, the blood flowing through the fistula and the blood coming from the capillary systems are finally re-united in the return to the heart. If on the other hand the extra-corporeal blood flow is more than the fistular flow, blood from the extra-corporeal blood circuit recirculates, with flow taking place through the fistula from the venous to the arterial connection.

To determine fistular recirculation and the cardio-pulmonary proportion of recirculation, the sum of fistular recirculation and the cardio-pulmonary proportion of recirculation, which is called recirculation R, is first determined. The control unit 17 first controls the means 20 to produce the temperature bolus, on the path II for the dialysis fluid, upstream of the dialysis-fluid chamber 9 of the dialyser 6, which means that the temperature of the dialysis fluid is changed, and raised for example, typically by approx. 2.5° C. for 2.5 minutes. After this, the desired temperature of the dialysate which applied at the beginning of the bolus is re-established.

The temperature bolus is transmitted via the dialyzer 6 into the extra-corporeal blood circuit I and in the blood circuit I it produces an increase or decrease in the temperature of the venous blood flowing from the dialyser 6 to the patient. The venous temperature sensor 21 senses this change in temperature. The venous temperature bolus which propagates due to fistular recirculation and cardio-pulmonary recirculation is sensed by the arterial temperature sensor 22 as an attenuated temperature bolus. The computing and analyzing unit 18 receives the measured values from the venous and arterial temperature sensors 21, 22 and stores them. The computing and analyzing unit 18 also receives the value for the blood flow rate $Q_B$ which is preset by the control unit 17. From the two measured values for the arterial and venous temperatures $T_A$ and $T_V$, the computing and analyzing unit 18 calculates the recirculation.

Figure 3:
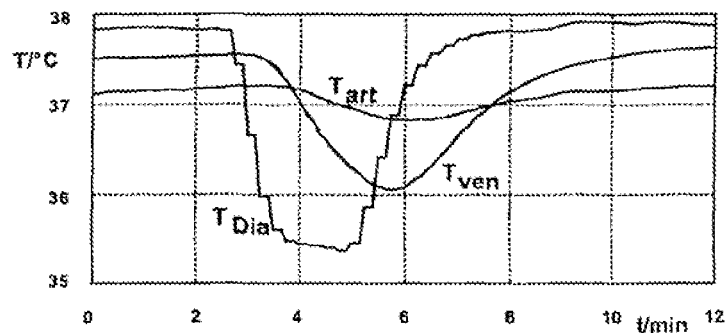
FIG. 3 is a plot against time of arterial and venous fistula temperature and dialysate temperature during a measurement of recirculation.

FIG. 3 shows the temperature $T_{DIA}$ of the dialysis fluid upstream of the dialyzer 6, and the temperatures $T_V$ and $T_A$ of the venous and arterial blood, as a function of time. The ratio of the size of the arterial response bolus $T_A$ to the size of the stimulating bolus $T_V$ corresponds to the sum of fistular recirculation and/or the cardio-pulmonary proportion of recirculation. The computing and analyzing unit 18 determines the sizes of the arterial and venous temperature boluses by integration or by way of their amplitudes and calculates the recirculation from the ratio of the two temperature integrals by methods known in the prior art. Because the determination of recirculation is part of the prior art, the method will not be described in detail. As a disclosure, reference is made for example to the method described in the EDTNA-ERCA Journal 19, 6 (1993), which method employs the principle of thermodilution. This method of measuring the total circulation which is made up of fistular recirculation and cardio-pulmonary recirculation is also described in Drukker, Parsons and Maher, Replacement of Renal Function by Dialysis, $5^{th}$ edition, 2004, Kluwer Academic Publishers BV. As well as this, it is also possible for the total recirculation to be determined for the two blood-flows by the method which is described in German Patent Application Publication No. DE 197 02 441 C1.

The present invention is based on determining recirculation by the known methods in a first method at a first blood flow rate $Q_{BH}$ and in a succeeding, second measurement at a second blood flow rate $Q_{BL}$, in which case the two blood flow rates differ from one another. One of the two blood flow rates, such for example as the first blood flow rate $Q_{BH}$, is of a size such that fistular recirculation $R_A$ occurs, whereas the other blood flow rate $Q_{BL}$ is of a size such that fistular recirculation does not occur.

Fistular recirculation occurs when the blood flow is greater than the fistular flow, i.e., more blood is drawn from the fistula than flows to it. By contrast, fistular recirculation does not occur when the fistular flow is appreciably greater than the blood flow. Empirical values can be used as values for the higher blood flow at which fistular recirculation occurs and the lower blood flow at which fistular recirculation does not occur. It can be assumed in this case that fistular flow under the conditions preset in practice is between 800 and 1000 ml/min, but generally not more than 1500 ml/min.

From the two values for the recirculations $R_H$, $R_L$, at the higher and lower blood flow rates $Q_{BH}$, $Q_{BL}$ at which fistular recirculation respectively does and does not occur, the computing and analyzing unit 18 calculates the fistular recirculation $R_A$, which is dependent on the blood flow rate. The computing and analyzing unit 18 then calculates the cardio-pulmonary proportion of recirculation $R_{CP}$ from the recirculation R determined for a preset blood flow rate and from the calculated fistular recirculation $R_A$.

The calculation of the fistular recirculation $R_A$ and the cardio-pulmonary proportion of recirculation $R_{CP}$ is performed by an approximation method which is sufficiently good in the context of the accuracy which is required in practice, which method will be described in detail in what follows.

Figure 2:
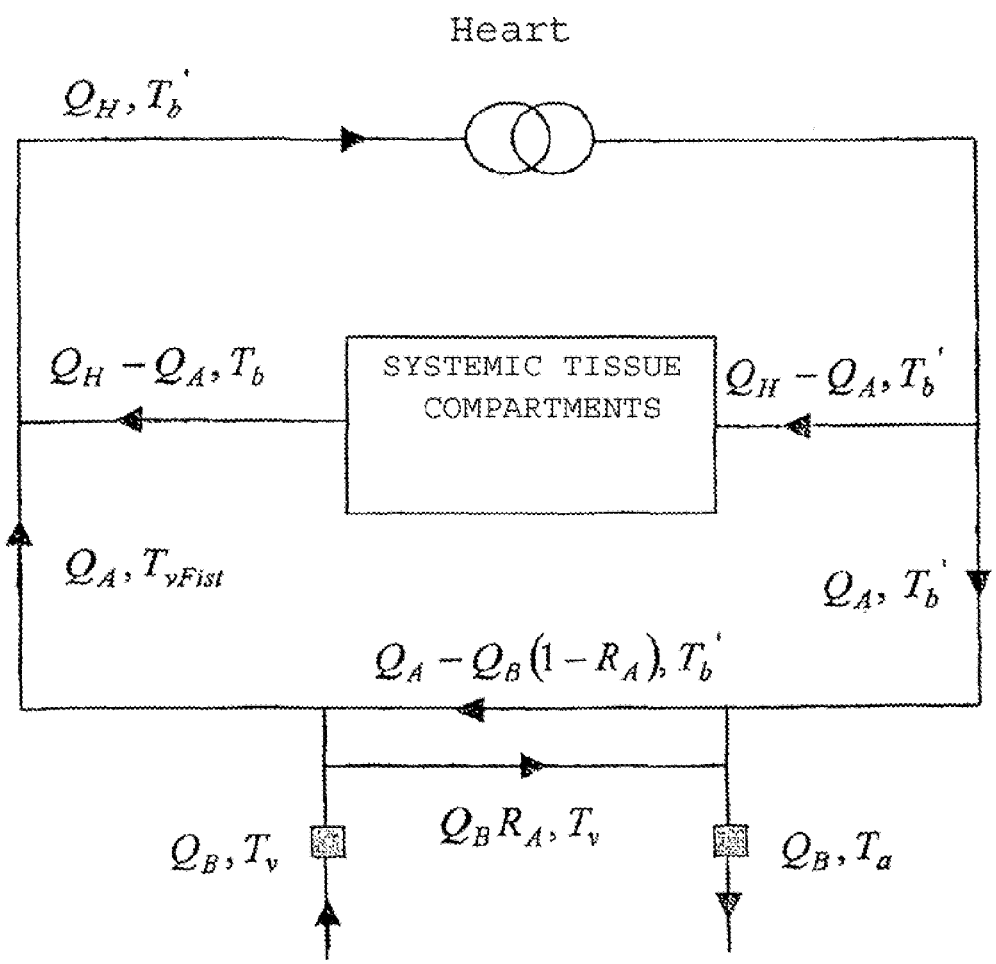
FIG. 2 is a schematic view showing the extra-corporeal and intra-corporeal blood circuits.

FIG. 2 is a simplified schematic representation of the flows and temperatures in the intra-corporeal and extra-corporeal circuits, where

| | |
|---|---|
| $Q_H$: | Cardiac output |
| $Q_A$: | Fistular flow |
| $Q_B$: | Blood flow |
| $Q_{RA}$: | Proportion of recirculating flow in the fistula |
| $R_A$: | Recirculation in the fistula |
| $R_{cp}$ | Cardio-pulmonary recirculation (proportion of cardiac output represented by fistula) |
| $R_b$ | Proportion of cardiac output represented by blood flow |
| $R_{CP}$: | Cardio-pulmonary proportion of recirculation |
| R: | Total recirculation in the extra-corporeal blood circuit |
| $R_H$: | Recirculation measured at a high blood flow $Q_{BH}$ |
| $R_L$: | Recirculation measured at a low blood flow $Q_{BL}$ |
| $T_v$: | Measured venous temperature of fistula |
| $T_a$: | Measured arterial temperature of fistula |
| $T_{vFistula}$: | Venous temperature of fistula |
| $T_b$: | Body temperature |
| $T_b'$: | Body temperature |
| $Q_{UF}$: | Ultrafiltration rate |

If recirculation occurs in the fistula, recirculation R as a whole is made up of the fistular and cardio-pulmonary proportions of recirculation:

The total recirculation R is that proportion of the blood flow $Q_B$ which is represented by the already cleaned extra-corporeal blood flow $Q_{already\ cleaned}$ which re-enters the extra-corporeal blood circuit via the arterial access without an equalisation of concentration having previously taken place in the (large) circuit in the body, ($Q_{already\ cleaned}/Q_B$).

The total recirculation R is made up of a proportion $R_{CP}$ of the flow of cleaned blood which passes back into the extra-corporeal blood circuit directly following the circuit through the lungs without there having previously been an equalisation of concentration in the large circuit in the body, and of the fistular recirculation $R_A$.

$$R = R_A + R_{CP} \tag{1}$$

The proportion $R_{CP}$ of the flow of cleaned blood is also referred to in the literature as cardio-pulmonary recirculation. However, what is also referred to in the literature as cardio-pulmonary recirculation is the proportion of cardiac output ($Q_H$) in the blood flow ($Q_A$) through the arterio-venous shunt ($R_{cp} = Q_A/Q_H$). To distinguish it from this blood flow, that proportion of the flow of cleaned blood which passes back into the extra-corporeal blood circuit directly following the circuit through the lungs without an equalization of concentration is referred to here as the cardio-pulmonary proportion of recirculation, i.e., as the proportion of cardio-pulmonary recirculation in the total recirculation $R_{CP}$. Schneditz states that this can be calculated from $R_{CP} = Q_B/(Q_H - Q_A + Q_B)$ (Schneditz et al., Seminars in Dialysis-Vol. 16 No. 6, 2003, pp. 483-487).

Fistular recirculation $R_A$ is also defined as that proportion of the extra-corporeal blood flow $Q_B$ which is represented by the dialyzed blood flow fed back to the fistula by the venous blood line and which is fed back again to the dialyzer via the arterial blood line because of a (partial) reversal of flow in the shunt ($R_A = Q_{Reversal\ of\ flow}/Q_B$).

The method of measuring recirculation which is known as thermodilution takes into account all the flows and temperatures which are shown in FIG. 2, it being assumed that there is no interchange with the surroundings. $T_b$ is the body temperature which arises from the micro-circulation in the systematic tissue compartments. $T_{vFist}$ is the temperature of the fistula. After the mixing with the fistular flow, a mixed body temperature $T_b'$ arises at which the blood makes its way to the heart and on to the fistula. Further temperature-mixing processes take place in the fistula.

Under the principle of heat balance, what applies is:

$$Q_H T_b' = (Q_H - Q_A) T_b + Q_A T_{vFist}$$

$$Q_A T_{vFist} = (Q_A - Q_B(1 - R_A)) T_b' + Q_B(1 - R_A) T_v$$

where $R_{cp} = Q_A/Q_H$ Proportion which fistular flow represents of cardiac output (=cardio-pulmonary recirculation)
and $R_b = Q_B/Q_H$ Proportion which blood flow represents of cardiac output $$T_b' = \frac{T_a - R_A T_v}{1 - R_A}$$

$$T_b = \frac{(1 - R_{cp} + R_b(1 - R_A)) T_b - R_b(1 - R_A) T_v}{1 - R_{cp}}$$

When inserted and changed to the following form $$T_b = \frac{T_a - R T_v}{1 - R}$$

$$R = \frac{R_b(1 - R_A) + R_A(1 - R_{cp})}{1 - R_{cp} + R_b(1 - R_A)}$$

With due allowance for the effect of ultrafiltration, the following equation is obtained, derived in a similar way from the principle of heat balance:

$$R = \frac{(R_b - R_{uf})(1 - R_A) + R_A\left(1 - \frac{Q_{uf}}{Q_B}\right)(1 - R_{cp} + R_{uf})}{1 - R_{cp} + R_b(1 - R_A) + R_A R_{uf}}$$

where $Q_{uf}$ is the ultrafiltration rate (ml/min) and $$R_{uf} = Q_{uf}/Q_H.$$

In practice, the effect of ultrafiltration is negligible. Hence, the above equation becomes $$R = \frac{R_b(1 - R_A) + R_A(1 - R_{cp})}{1 - R_{cp} + R_b(1 - R_A)} \text{ when } Q_{uf} = 0.$$

In the event of fistular recirculation not occurring ($R_A=0$):

$$R = \frac{R_b}{1 - R_{cp} + R_b} = \frac{Q_B}{Q_H - Q_A + Q_B} \quad (2)$$

After a conversion $$R = \frac{R_b(1 - R_A) + R_A(1 - R_{cp})}{1 - R_{cp} + R_b(1 - R_A)},$$

of what is obtained is $$R = \frac{Q_b(1 - R_A) + R_A(Q_H - Q_A)}{Q_H - Q_A + Q_B(1 - R_A)} \quad (3)$$

From the first measurement of recirculation at the low blood flow of $Q_{BL}$, assuming $R_A=0$:

$$R_L = \frac{Q_{BL}}{Q_H - Q_A + Q_{BL}} \quad (4)$$

$$Q_H - Q_A = \frac{1 - R_L}{R_L} \cdot Q_{BL}$$

From the second measurement of recirculation at the high blood flow of $Q_{BH}$, assuming $R_A \neq 0$:

$$R_H = \frac{Q_{BH}(1 - R_A) + R_A(Q_H - Q_A)}{Q_H - Q_A + Q_{BH}(1 - R_A)} \quad (5)$$

From (4) and (5), $$R_A = \frac{(1 - R_L)R_H k - R_L(1 - R_H)}{(1 - R_L)k - R_L(1 - R_H)} \quad (6)$$

where $k = \frac{Q_{BL}}{Q_{BH}}$.

After the first and second measurements of recirculation to determine recirculation, the computing and analyzing unit 18 calculates fistular recirculation $R_A$, on the assumption that $R_A$ is equal to zero and on the assumption that $R_A$ is not equal to zero, from the mean values for $R_L$ and $R_H$ and from the low blood flow $Q_{BL}$ for $R_A$ equal to zero and the high blood flow $Q_{BH}$ for $R_A$ not equal to zero, using equation (6).

The computing and analyzing unit 18 then calculates, from equation (1), the cardio-pulmonary proportion of recirculation $R_{CP}$ as a function of the blood flow $Q_B$. For this purpose, the computing and analyzing unit forms the difference between the recirculation R measured for a given blood flow $Q_B$, such as for example the recirculation measured in the preceding first measurement of recirculation, and the fistular recirculation $R_A$ calculated previously.

The two values, for fistular recirculation $R_A$ and the cardio-pulmonary proportion of recirculation $R_{CP}$, are shown on a indicator unit 23, such as a display for example, which is connected to the computing and analyzing unit 18 by a data line 24.

From the values determined for the fistular recirculation $R_A$ and the cardio-pulmonary proportion of recirculation $R_{CP}$, further values which are relevant to the dialysis treatment can be calculated in the computing and analyzing unit, using equations which are known from the prior art.

An alternative embodiment makes provision for the analysis described below of the measured results.

The cardio-pulmonary proportion of recirculation $R_{CP}$ is calculated by the Schneditz formula (Schneditz D, Kaufman A M, Levin N: Surveillance of access function by the blood temperature monitor, Semin Dial 16(6) (2003) 483-7), on the assumption that recirculation does not occur in the fistula, from the following equation:

$$R_{CP} = \frac{Q_B}{Q_H - Q_A + Q_B} \quad (7)$$

If fistular recirculation does occur, the whole of the recirculation is calculated from the sum of the fistular recirculation $R_A$ and the cardio-pulmonary proportion of recirculation $R_{CP}$:

$$R = R_A + R_{CP} \quad (8)$$

The first measurement of recirculation at a high blood flow $Q_{BH}$ (it is possible for fistular recirculation to occur):

$$R_H = \frac{Q_{RA}}{Q_{BH}} + \frac{Q_{BH} - Q_{RA}}{Q_H - Q_A + (Q_{BH} - Q_{RA})} \quad (9)$$

$$= \frac{Q_{RA}}{Q_{BH}} + \frac{1 - Q_{RA}/Q_{BH}}{(Q_H - Q_A)/Q_{BH} + (1 - Q_{RA}/Q_{BH})}$$

$$R_H = R_A + \frac{1 - R_A}{(Q_H - Q_A)/Q_{BH} + (1 - R_A)}$$

The second measurement of recirculation at a low blood flow $Q_{BL}$ (fistular recirculation does not occur):

$$R_L = \frac{Q_{BL}}{Q_H - Q_A + Q_{BL}} \quad (10)$$

$$Q_H - Q_A = Q_{BL} \cdot \left(\frac{1}{R_L} - 1\right)$$

From (9) and (10):

$$R_A^2 - (R_H + k) \cdot R_A + R_H(1 + k) - 1 = 0 \quad (11)$$

where $k = \frac{Q_{BL}}{Q_{BH}} \cdot \left(\frac{1}{R_L} - 1\right)$

The sensible solution of equation (11) is $$R_A = 0.5 \left[R_H + k - \sqrt{(k - R_H)^2 + 4(1 - R_H)}\right] \quad (12)$$

In the alternative embodiment, after making the two measurements of recirculation for determining the recirculations $R_H$ and $R_L$ at a high and a low blood flow $Q_{BH}$ and $Q_{BL}$ at which fistular recirculation does and does not occur, the computing and analyzing unit 18 calculates the fistular recirculation $R_A$ from equation (12).

Then, for a given blood flow $Q_B$, the computing and analyzing unit 18 calculates the cardio-pulmonary proportion of recirculation $R_{CP}$ from the recirculation R determined for this blood flow and from the fistular recirculation $R_A$ which has been calculated, using equation (8).

Basically, the second measurement of a physical or chemical parameter in the blood at a low blood flow rate can be dispensed with if, as a result of the first measurement which is made at a higher blood flow rate, the occurrence of fistular recirculation can be estimated to be unlikely. An alternative example embodiment therefore makes provision for periodic measurements of a physical or chemical parameter in the blood at a higher flow rate $Q_{BH}$ to determine the sum of fistular recirculation and the cardio-pulmonary proportion of recirculation, i.e. total recirculation, a second measurement of the physical or chemical parameter taking place at a lower blood flow only if a preset limiting value is exceeded at the time of the first measurement. The preset limiting value may be a value which is based on empirical figures. What can be used as a limiting value is the bottom limit of the cardio-pulmonary proportion of recirculation $R_{CP}$, which is for example 5 to 10% and in particular is 6-8%. Other empirical values may also be used however. This alternative example embodiment constitutes a particular inventive concept that falls within the scope of the present invention.

The invention claimed is:

1. An arrangement for determining recirculation ($R_A$) in a fistula and/or the cardio-pulmonary proportion of recirculation ($R_{CP}$), for a blood-treating apparatus in which the blood to be treated flows in an extra-corporeal blood circuit through a blood chamber of a dialyzer which is divided into the blood chamber and a dialysis-fluid chamber by a semi-permeable membrane and dialysis fluid flows through the dialysis-fluid chamber of the dialyzer on a path for dialysis fluid, a blood pump being arranged in the extra-corporeal blood circuit, the arrangement comprising:
a control unit configured to control first and second changes in a physical or chemical parameter in the blood, wherein the control unit is configured to set first and second blood flow rates to values such that fistula recirculation ($R_A$) occurs at a value of the first blood flow rate but does not occur at a value of the second blood flow rate;
a sensor configured to a) measure, in the blood, the first change in the physical or chemical parameter at the first blood flow rate ($Q_{BH}$), and b) measure, in the blood, the second change in the physical or chemical parameter at the second blood flow rate ($Q_{BL}$), the first and second blood flow rates being different from one another; and
a computing and analyzing unit configured to determine the fistular recirculation ($R_A$) and/or the cardio-pulmonary proportion of recirculation ($R_{CP}$) on the basis of the physical or chemical parameter that is measured at the first and second blood flow rates ($Q_{BH}$, $Q_{BL}$).

2. The arrangement according to claim 1, wherein the computing and analyzing unit is configured to a) determine the sum ($R_H$) of fistular recirculation and the cardio-pulmonary proportion of recirculation for the first blood flow rate on the basis of the physical or chemical parameter which is measured at the first blood flow rate ($Q_{BH}$), and b) determine the sum ($R_L$) of fistular recirculation and the cardio-pulmonary proportion of recirculation for the second blood flow rate on the basis of the physical or chemical parameter which is measured at the second blood flow rate ($Q_{BL}$).

3. The arrangement according to claim 2, wherein the computing and analyzing unit is configured to determine the fistular recirculation ($R_A$) from the sums ($R_H$ and $R_L$), as determined at the first and second blood flow rates ($Q_{BH}$ and $Q_{BL}$), of the cardio-pulmonary proportion of recirculation ($R_P$) and fistular recirculation ($R_A$), from the following equation:

$$R_A = \frac{(1-R_L)R_H k - R_L(1-R_H)}{(1-R_L)k - R_L(1-R_H)}$$

where $k = \dfrac{Q_{BL}}{Q_{BH}}$.

4. The arrangement according to claim 2, wherein the computing and analyzing unit is configured to determine the fistular recirculation ($R_A$) from the sums ($R_H$ and $R_L$), as determined at the first and second blood flow rates ($Q_{BH}$ and $Q_{BL}$), of the cardio-pulmonary proportion of recirculation ($R_{CP}$) and fistular recirculation ($R_A$), from the following equation:

$$k = \frac{Q_{BL}}{Q_{BH}} \cdot \left(\frac{1}{R_L} - 1\right)$$

$$R_A = 0.5\left[R_H + k - \sqrt{(k-R_H)^2 + 4(1-R_H)}\right].$$

5. The arrangement according to claim 3, wherein the computing and analyzing unit is configured to determine the difference between a) the sum of the cardio-pulmonary proportion of recirculation ($R_{CP}$) and fistular recirculation ($R_A$), and b) the fistular recirculation ($R_A$).

6. The arrangement according to claim 1, wherein the control unit is configured to control the temperature of the blood.

7. The arrangement according to claim 6, wherein the sensor is configured to measure the temperature of the blood.

8. A blood-treating apparatus, comprising:
an arrangement for determining fistular recirculation ($R_A$) and/or the cardio-pulmonary proportion of recirculation ($R_{CP}$) according to claim 1;
a dialyzer which is divided into a blood chamber and a dialysis-fluid chamber by a semi-permeable membrane;
an extracorporeal blood circuit including an arterial blood line which leads to the blood chamber of the dialyzer, and a venous blood line which runs from the blood chamber;
a blood pump arranged in the extra-corporeal blood circuit,
a dialysis-fluid infeed line configured to provide dialysis fluid to the dialysis-fluid chamber of the dialyzer; and
a dialysis-fluid takeaway line configured to take dialysis fluid away from the dialysis-fluid chamber of the dialyzer.

* * * * *